United States Patent [19]

Blythin et al.

[11] Patent Number: 5,011,845

[45] Date of Patent: Apr. 30, 1991

[54] CYCLIC DIESTERS OF 4-HYDROXY-1,3-BENZENEDIMETHANOL AND COMPOSITIONS AND METHODS EMPLOYING SUCH COMPOUNDS

[75] Inventors: David J. Blythin, North Caldwell; Ho-Jane Shue, Pine Brook; Ashit K. Ganguly, Upper Montclair, all of N.J.

[73] Assignee: Schering Corporation, Kenilworth, N.J.

[21] Appl. No.: 537,385

[22] Filed: Jun. 13, 1990

[51] Int. Cl.[5] .................. A61K 31/44; A61K 31/365; C07D 321/00; C07D 498/14

[52] U.S. Cl. .................................... 514/291; 549/42; 549/43; 549/44; 549/45; 549/267; 549/343; 549/345; 546/89; 546/90; 546/62; 514/250; 514/287; 514/450; 514/443; 514/826

[58] Field of Search .................. 549/267, 268, 43, 44, 549/45, 42; 546/89, 90, 62; 544/345, 343; 514/450, 443, 250, 291, 826, 287

[56] References Cited

U.S. PATENT DOCUMENTS

| | | | |
|---|---|---|---|
| Re. 30,241 | 3/1980 | Minatoya et al. | 560/160 |
| 3,644,353 | 2/1972 | Leats et al. | 564/441 |
| 3,904,671 | 9/1975 | Minatoya et al. | 560/106 |

FOREIGN PATENT DOCUMENTS

| | | | |
|---|---|---|---|
| 1298771 | 12/1972 | United Kingdom | 560/106 |

*Primary Examiner*—Richard L. Raymond
*Assistant Examiner*—Mark W. Russell
*Attorney, Agent, or Firm*—Matthew Boxer; James R. Nelson

[57] ABSTRACT

Compounds of the formula

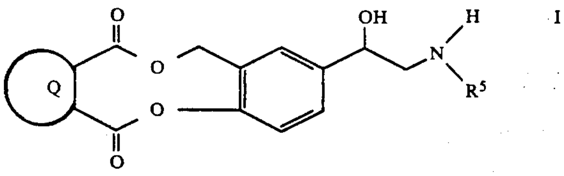

I wherein $R^5$ represents $C_1$ to $C_6$-alkyl or the group—$(CH_2)_n$—Z—$(CH_2)_m$—Ar wherein Z represents O, S or —$CH_2$—and Ar is phenyl, optionally substituted by one or two groups selected from the group consisting of hydrogen, $C_1$ to $C_6$-alkyl, $C_1$ to $C_6$-alkoxy, Cl,F,Br,I,$NO_2$, $CF_3$, CN, $R^6$-$S(O)_x$, $R^7$—CO—,$(R^8R^9)$NCO-and phenyl, wherein x is 0, 1 or 2, and each $R^6$, $R^7$, $R^8$ and $R^9$ is independently $C_1$ to $C_6$ alkyl or two adjacent groups on Ar may form together an additional fused benzenoid ring; n and m independently represent integers of from 1 to 8; and ring Q represents one of the rings $Q_1$, $Q_2$, $Q_3$ or $Q_4$ below:

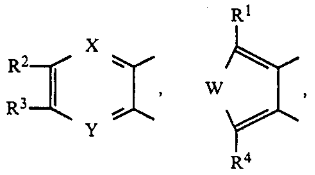

$Q_1$ $Q_2$

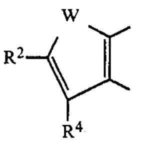

or

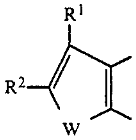

;

$Q_3$ $Q_4$

X is N or C—$R^1$;
Y is N or C—$R^4$;
W represents O or S;

each of $R^1$, $R^2$, $R^3$ and $R^4$ is independently selected from hydrogen, $C_1$ to $C_6$-alkyl, $C_1$ to $C_6$-alkoxy, Cl,F,Br,I,-$NO_2$,$CF_3$,CN, $R^{10}$-$S(O)_y$—, $R^{11}$—CO—, $(R^{12}R^{13})$N—CO—or phenyl, wherein y is 0, 1 or 2 and each of $SR^{10}$, $R^{11}$, $R^{12}$ and $R^{13}$ is independently $C_1$ to $C_6$-alkyl, or, in the ring $Q_1$, two adjacent groups, i.e. $R^1R^2$, $R^2R^3$ or $R^3R^4$, may form together an additional fused benzenoid ring; and pharmaceutically acceptable acid addition salts of such compounds are described.

These compounds provide favorable properties for the treatment of asthma and all types of chronic, obstructionary bronchopulmonary diseases.

18 Claims, No Drawings

CYCLIC DIESTERS OF 4-HYDROXY-1,3-BENZENEDIMETHANOL AND COMPOSITIONS AND METHODS EMPLOYING SUCH COMPOUNDS

BACKGROUND OF THE INVENTION

This invention relates to certain cyclic di-esters of known $\beta_2$-agonists, which di-esters possess favorable properties for the treatment of asthma and all types of chronic obstructionary pulmonary diseases (COPD).

$\beta_2$-agonists are well known in the art, e.g. albuterol which is described in U.S. Pat. No. 3,644,353. Certain esters of albuterol or compounds closely related to albuterol have also been described, e.g. in U.S. Re. Pat. No. 30 241, British Patent No. 1,298,771, U.S. Pat. No. 3,904,671. However, none of these publications describe or suggest the cyclic di-esters of this invention.

SUMMARY OF THE INVENTION

The compounds of this invention are of the formula I

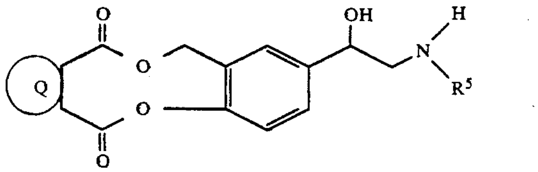

I wherein $R^5$ represents $C_1$ to $C_6$-alkyl or the group $-(CH_2)_n-Z-(CH_2)_m-Ar$ wherein Z represents O, S or $-CH_2-$ and Ar is phenyl, optionally substituted by one or two groups selected from the group consisting of hydrogen, $C_1$ to $C_6$-alkyl, $C_1$ to $C_6$-alkoxy, Cl, F, Br, I, $NO_2$, $CF_3$, CN, $R^6-S(O)_x$, $R^7-CO-$, $(R^8R^9)NCO-$ and phenyl, wherein x is 0, 1 or 2, and each $R^6$, $R^7$, $R^8$ and $R^9$ is independently $C_1$ to $C_6$ alkyl or two adjacent groups on Ar may form together an additional fused benzenoid ring; n and m independently represent integers of from 1 to 8; and ring Q represents one of the rings $Q_1$, $Q_2$, $Q_3$ or $Q_4$ below:

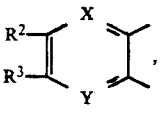

,

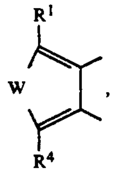

, $Q_1$ $Q_2$

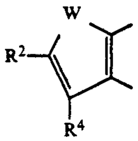

or

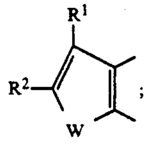

;

$Q_3$ $Q_4$

X is N or $C-R^1$;

Y is N or $C-R^4$;

W represents O or S;

each of $R^1$, $R^2$, $R^3$ and $R^4$ is independently selected from hydrogen, $C_1$ to $C_6$-alkyl, $C_1$ to $C_6$-alkoxy, Cl, F, Br, I, $NO_2$, $CF_3$, CN, $R^{10}-S(O)_y-$, $R^{11}-CO-$, $(R^{12}R^{13})NCO-$ or phenyl, wherein y is 0, 1 or 2 and each of $R^{10}$, $R^{11}$, $R^{12}$ and $R^{13}$ is independently $C_1$ to $C_6$-alkyl, or, in the ring $Q_1$, two adjacent groups, i.e. $R^1R^2$, $R^2R^3$ or $R^3R^4$, may form together an additional fused benzenoid ring;

and pharmaceutically acceptable acid addition salts of such compounds.

The compounds of the invention are preferably in the form of pharmaceutically acceptable acid addition salts.

The preferred meaning of $R^5$ is i-$C_3H_7$, t-$C_4H_9$ or $-(CH_2)_n-Z-(CH_2)_m-Ar$ wherein n and m each independently is an integer of 2 to 6, Z represents O and Ar is phenyl.

Q preferably represents the ring $Q_1$.

$Q_1$ preferably is

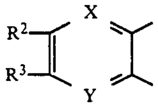

wherein X is N or $C-R^1$, and Y is N or $C-R^4$ with the proviso that X and Y are not both N; each of $R^1$, $R^2$, $R^3$ and $R^4$ is independently selected from hydrogen, $C_1$ to $C_6$-alkyl, $C_1$ to $C_6$-alkoxy, Cl, F, Br, I, $NO_2$, $CF_3$, CN, $R^{10}-S(O)_y-$, $R^{11}-CO-$, $R^{12}R^{13}N-CO-$ or phenyl, wherein y is 0, 1 or 2 and each $R^{10}$, $R^{11}$, $R^{12}$ and $R^{13}$ is independently $C_1$ to $C_6$-alkyl, or, in the ring $Q_1$, two adjacent groups, i.e. $R^1R^2$, $R^2R^3$ or $R^3R^4$, may form together an additional fused benzenoid ring.

Even more preferred are compounds as described just above wherein one or two of $R_1$, $R_2$, $R_3$, and $R_4$ are independently selected from F, Cl, $CF_3$, $CH_3$ and $C_2H_5$ and the remainder of these substituents are H.

Also preferred are compounds of formula I wherein Q represents the ring $Q_2$ or ring $Q_3$ or $Q_4$.

Another preferred embodiment relates to compounds of formula I wherein Q represents the ring

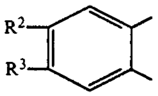

$Q_1$ wherein one of $R^2$ and $R^3$ is hydrogen and the other is H, F, Cl, $CF_3$, $CH_3$ or $C_2H_5$.

Still another preferred embodiment involves compounds of formula I wherein Q represents the ring

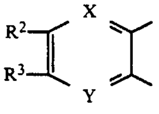

$Q_1$ and wherein either Y is $C-R^4$ and X is N; or X is $C-R^1$ and Y is N and $R^1$ and $R^4$ are H, F, Cl, $CF_3$, $CH_3$ or $C_2H_5$.

Especially preferred compounds are those having the following configuration at the carbon atom indicated by *:

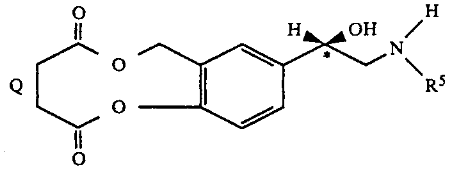

wherein $R^5$ is as described above.

The compounds of formula I provide bronchodilating activity and accordingly are useful in the treatment of chronic obstructionary pulmonary diseases such as asthma.

The invention also involves pharmaceutical compositions comprising a compound of formula I above in salt form in combination with a pharmaceutically acceptable carrier and methods of treating asthma, asthmatic bronchitis and other forms of obstructive pulmonary disease by administering an effective amount of a compound of formula I above for such purpose.

DETAILED DESCRIPTION OF THE INVENTION

The following term used in the specification and claims has the meaning indicated below, unless otherwise indicated:

alkyl (including the alkyl portions of alkoxy, alkylthio, etc.) - represents a straight or branched, saturated hydrocarbon chain having the number of carbon atoms designated. For example, $C_1$ to $C_6$ alkyl is a straight or branched chain alkyl of 1 to 6 carbon atoms.

Preferred compounds include:

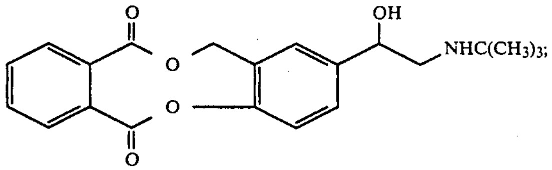

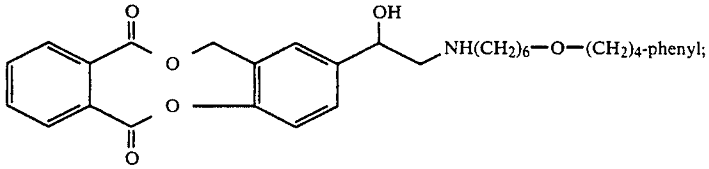

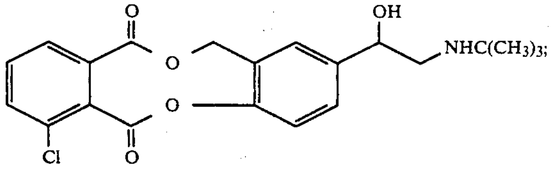

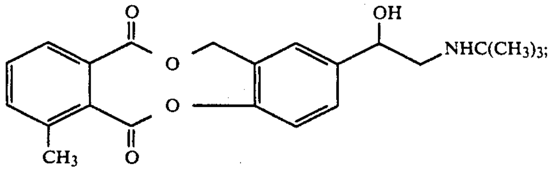

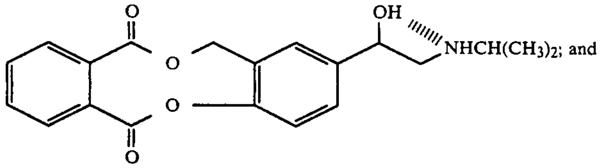

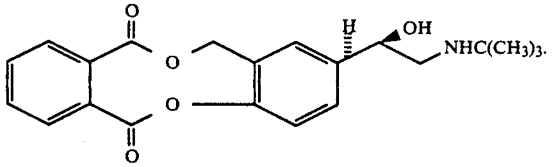

The most preferred compounds are:

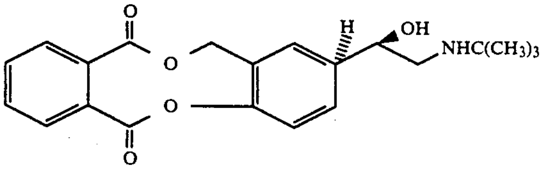

and

-continued

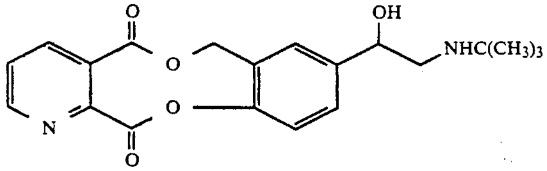

Certain compounds of this invention may exist in isomeric forms. The invention contemplates all such isomers both in pure form and in admixture, including racemic mixtures.

All compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

The compounds of the invention form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms differ from their respective salt forms somewhat in certain physical properties, such as solubility in polar solvents, but the salts are otherwise equivalent to their respective free base forms for purposes of this invention.

The compounds of this invention may be prepared according to methods well known for preparation of compounds with a similar structure:

A: An alcohol of the formula II

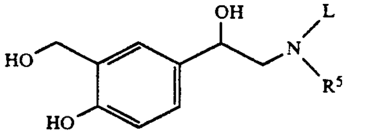
II wherein $R^5$ is as described above and L represents a protecting group, such as benzyl, alkyl or alkoxy substituted benzyl, or benzhydryl; is reacted with an acid chloride of the formula III

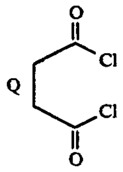
III wherein Q is as described above for formula I, to yield a compound of formula IV

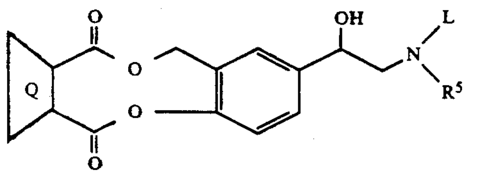
IV wherein Q, L and $R^5$ are as described above, followed by removal of the protecting group L as described below. The reaction is conducted in a suitable solvent such as $CH_2Cl_2$ at a temperature in the range of about 0° to about −78° C. in the presence of a base such as triethylamine or diisopropylethylamine. The addition of a catalytic quantity of dimethylaminopyridine (DMAP) may aid the reaction, depending on the structure of the diacid chloride. The resulting compound of formula IV can be used without purification in the next step. The second reaction is carried out in a mixture of an alcohol, preferably isopropanol and a halogenated solvent, preferably $CH_2Cl_2$. An equivalent amount, or a slight excess of acid, preferably $CF_3CO_2H$ is added to the solution of substrate and to the mixture is added a suitable catalyst, preferably 2–10% Pd-C (palladium on charcoal). The stirred suspension is hydrogenolyzed in an atmosphere of hydrogen, following the conversion of starting material from time to time by thin layer chromatography.

B. An alcohol of formula II is reacted with an acid anhydride of the formula V

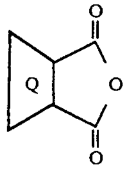
V wherein Q is as described above, to yield a monoester of the formula VI

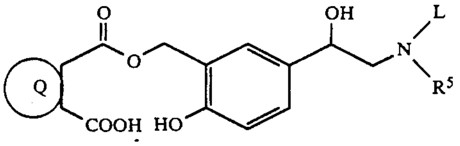
VI wherein Q, L and $R^5$ are as described above, followed by a second esterification step yielding a compound of formula IV, which compound is further treated as under A above. The first esterification step is conducted in a suitable solvent such as pyridine or more preferably $CH_2Cl_2$ at a temperature from about −78° C. to about 0° . The second esterification step is conducted in a suitable solvent such as $CH_2Cl_2$. It is further conducted in the presence of an acid anhydride, such as trifluoracetic anhydride, and an organic base, such as triethylamine at a temperature of from about −10° C. to about 25° C. This step may also be conducted in the presence of 1,3-dicyclohexylcarbodiimide. The L group is removed as described below.

C: A compound of the formula VII

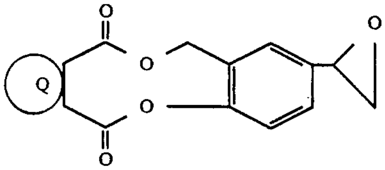
VII wherein Q is as described above, may also be reacted with a compound of the formula

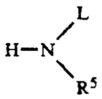

VIII wherein $R^5$ and L are as described above to yield a compound of formula IV followed by removal of the protecting group L as described below. The reaction is conducted in a solvent such as an alcohol or dimethylformamide, toluene or more preferably in a mixture of isopropanol and $CH_2Cl_2$, at a suitable temperature such as room temperature in the presence of a hydrogenation catalyst such as 10% Pd-C under about 1 atmosphere $H_2$. Isolation of the resulting compound of formula I can be by conventional means such as column chromatography.

D: The L group of a compound of the formula IX

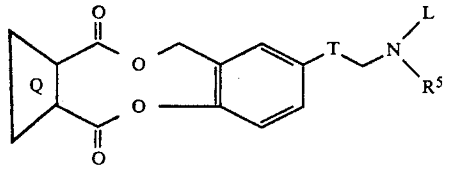

IX wherein Q, L and $R^5$ are as described above and T represents C═O, may be removed and the carbonyl group, represented by T, reduced to —CH(OH)—, to yield a compound of formula I.

The starting compounds used in the processes A to D above are either known compounds or may be obtained by reaction steps well known in the art for preparing similar compounds.

The alcohols of formula II may be prepared according to the following reaction schemes:

(i)

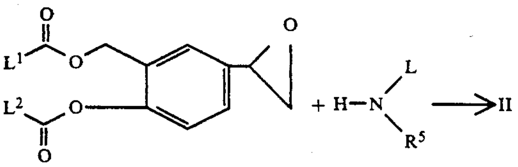

X VIII ($R^5$ and L are as described for formula II and $L^1$ and $L^2$, together with the carbonyl groups to which they are attached, represent conventional protecting groups, such as acetyl or benzoyl). This reaction is conducted in a solvent such as dimethylformamide, toluene, or more preferably $CH_2Cl_2$ at a temperature from about −10° to about 30°. The protecting groups $L^1$(CO)— and $L^2$(CO)— are then removed by conventional methods to yield a compound of formula II.

(Compounds of formula X are well known in the art, e.g. from British Patent No. 2 140 800 A.)

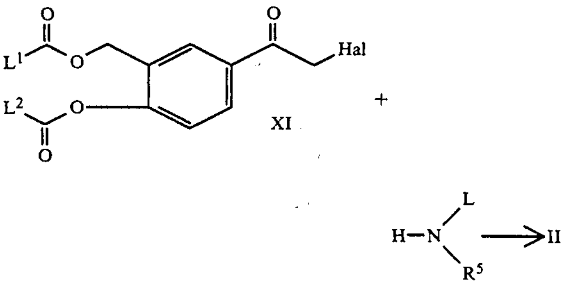

XI

VIII wherein $R^5$, L, $L^1$ and $L^2$ are as described above and Hal is halogen, preferably Cl or Br. This reaction is conducted in a solvent such as dimethylformamide, toluene, or more preferably $CH_2Cl_2$ at a temperature from about −10° to about 30°. The reaction of process D above, i.e. the removal of the protective group L and the reduction of the carbonyl function represented by T can be carried out in one or two steps. The one step reaction, which is preferred, comprises a single step hydrogenolysis/carbonyl reduction using metal catalysts, e.g. 5–10% Pd-C under an atmosphere of hydrogen in a solvent, e.g., a mixture of isopropanol and methylene chloride. In the two step process, the carbonyl group is reduced, and the protecting groups are removed as described in (i) above, to yield a compound of formula II.

The acid chlorides and anhydrides of formulae III, V, and VIII respectively, are well known in the art, or may be prepared by standard methodologies.

The starting compound of formula VII may be obtained by the following reaction steps:

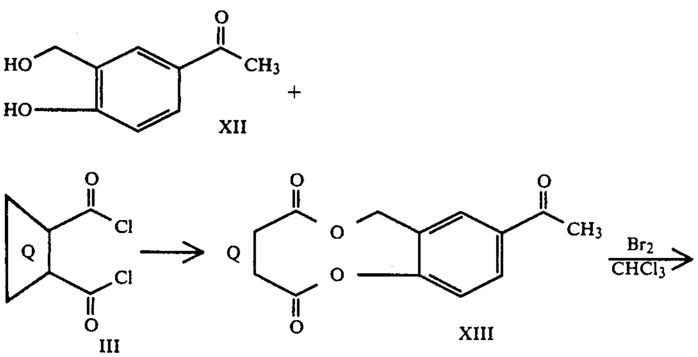

XII

III

XIII

-continued

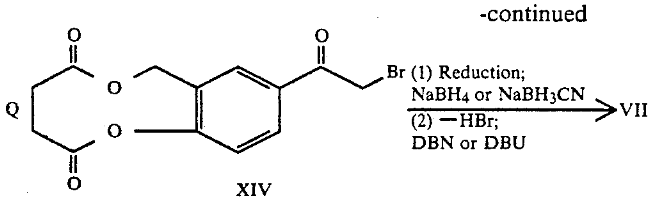

XIV wherein Q is as described above.

DBN is 1,5-diazabicyclo[4.3.0]non-5-ene.

DBU is 1,8-diazabicyclo[5.4.0]undec-7-ene.

Compounds of formula IX may be obtained by careful reaction of compound XIV with an amine of formula VIII at low temperature (0° C. to −78° C.). The reaction is conducted in a solvent such as dimethylformamide, toluene, or more preferably $CH_2Cl_2$. The resulting compound of formula IX can be isolated by conventional means such as column chromatography.

Compounds of formula IX may also be obtained by esterification reactions as described in processes A and B above, by reacting the acid chlorides III or anhydrides V, with a ketone of formula XV:

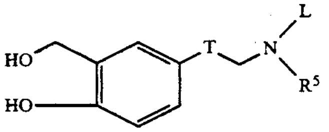

XV wherein T, L and $R^5$ are as described above.

The compounds of Formulae XII and XV are known or can be prepared by methods known in the art.

The compounds of the invention provide bronchodilating activity with enhanced duration of activity compared to the known unprotected diols. Such enhanced duration of activity varies with the Q groups employed.

The bronchodilator activity provided by the compounds of the invention may be demonstrated by the following test protocol.

INHIBITION OF HISTAMINE INDUCED BRONCHOSPASM

Procedure

Male Charles River Hartley strain guinea pigs are fasted overnight but allowed $H_2O$ ad lib. At −20 minutes, the animals are anesthetized with I.P. dialurethane. About 4 minutes later, the animals are shaved in the neck area and placed on their backs on a platform, inclined head up at 45° from horizontal. An incision is made through the skin and muscle/fascia teased apart to expose the trachea. Forceps are placed behind the trachea to hold it rigid while a 25 g $\frac{5}{8}$″ needle attached to a 1 cc syringe is inserted between cartilage rings pointing caudally into the lumen of the trachea and 0.2 mL of control vehicle (saline) or test compound (3 μg in 0.2 mL) is injected slowly intratracheally at −15 minutes. The needle and forceps are removed and the animal is transferred to a platform inclined at about 30° from horizontal (still on its back) and surgically prepared by installing an intratracheal tube. The animal is respirated during surgery. The animals are then transferred to a different respirator and monitored for insufflation pressure using a side-arm pressure transducer. Pump volume is 4.0 mL and the rate is 55 strokes/min. The animals are challenged at 0 minutes with an I.V. 10 μg/kg histamine (HA) bolus. A second I.V. HA challenge is given at +30 minutes (i.e. 45 minutes post I.T.) drug treatment.

Separate studies are conducted to determine whether bronchodilator activity lasts 3 hours. In these studies, the animals are first anesthetized with the short acting ingredient Brevital. Under anesthesia, the trachea is exposed and the compound is given, (15 μg in 0.2 mL) as described above. The animal recovers from the anesthesia within 30 minutes and is allowed free movement for the next 2 hours. At that time, the animals are anesthetized with dialurethane and surgically prepared for the measure of insufflation pressure and I.V. challenge with histamine (3 hours after drug treatment) as described above.

Results obtained in the above procedures are shown in Table 1 and expressed as a percent inhibition of the bronchospasm (increased insufflation pressure) due to histamine.

TABLE 1

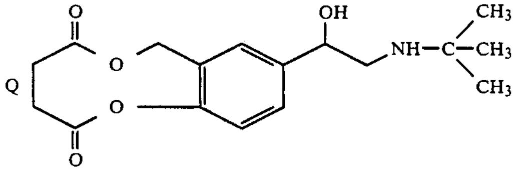

| ring Q | Activity at 15 min. | Activity at 45 min. | Activity at 3 hrs. |
|---|---|---|---|
| 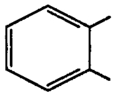 | 76 | 53 | 42 |
| 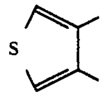 | 48 | 11 | — |
| 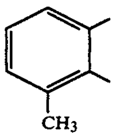 | 69 | 42 | 0 |
| 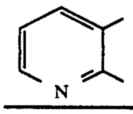 | 79 | 49 | 42 |

The active compounds can be administered orally, but are preferably delivered via aerosol, e.g., via oral or nasal inhalation.

The compounds can be administered in conventional oral dosage forms such as capsules or tablets prepared with conventional pharmaceutically acceptable excipients and additives, using conventional techniques. The oral dosage can be a total of about 2 to about 20 mg daily for an adult patient. Preferably, this total amount can be given as divided dosages such as two 10 mg capsules per day. Inhalation administration can be in the form of a nasal or oral spray. Insufflation is also contemplated.

For preparing pharmaceutical compositions from the compounds described by this invention, inert, pharmaceutically acceptable carriers can be either solid or liquid. Solid form preparations include powders, tablets or capsules. The powders and tablets may comprise from about 5 to about 70 percent active ingredient. Suitable solid carriers are known in the art, e.g., magnesium carbonate, magnesium stearate, talc, sugar, lactose.

Aerosol preparations suitable for inhalation may include solutions and solids in powder form, which may be in combination with a pharmaceutically acceptable carrier, such as an inert compressed gas. Normally, the formulation will be delivered from a dispensing or inhaling device, which would provide the preferred metered dose of the compound of the invention.

Preferably, the pharmaceutical preparation is in aerosol form. In such form, the preparation is delivered as unit doses containing appropriate quantities of the active component, e.g., an effective amount to achieve the desired purpose. When used in this way for the treatment of bronchoconstriction, the compounds of the invention can be administered in an amount ranging from about 50 μg to about 1000 μg per puff, preferably about 100 μg to about 500 μg per puff. A typical recommended dosage regimen is administration of from about 100 to about 2000 μg/day, preferably from about 200 to about 1000 μg/day, ("by inhalation") in two to four doses to achieve relief of the symptoms of bronchoconstriction.

Determination of the proper dosage of a compound of the invention for a particular situation is within the skill of the art. Generally, treatment is initiated with smaller dosages that are less than the optimum dose of the compound, Thereafter, the dosage is increased by small increments until the optimum effect under the circumstances is reached. For convenience, the total daily dosage may be divided and administered in portions during the day if desired.

The amount and frequency of administration of the compounds of formula I and the pharmaceutically acceptable salts thereof will be regulated according to the judgment of the attending clinician considering such factors as age, condition and size of the patient as well as severity of the symptoms being treated.

The invention disclosed herein is exemplified by the following preparative examples, which should not be construed to limit the scope of the disclosure. Alternative mechanistic pathways and analogous structures within the scope of the invention will be apparent to those skilled in the art.

EXAMPLE 1

Preparation of
2-[2-[(1,1,-Dimethylethyl)amino]-1-hydroxyethyl]-13H-dibenzo[b,g][1,5]-dioxonin-6,11-dione, acetic acid salt, 2.5 hydrate.

Method A (i)

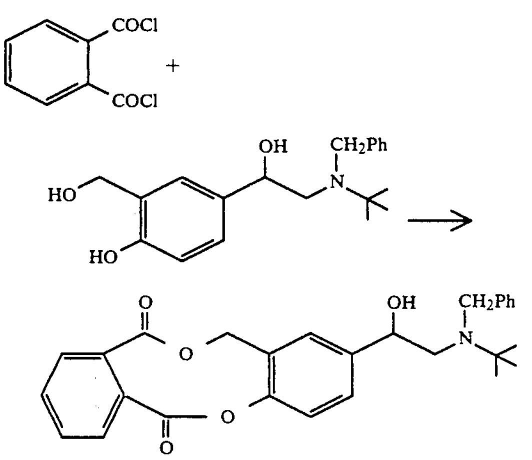

N-Benzyl-N-t-butyl-1-[2-hydroxy-5-hydroxymethyl] phenethylamine (10.0 g) was dissolved in $CH_2Cl_2$ (anhydrous, 400 mL) and chilled to below about −70° C. Triethylamine (10.6 mL, 2.5 eq; distilled) was added. When the internal temperature fell to −78° C. phthaloyl dichloride (5.06 mL, 1.1 eq) in $CH_2Cl_2$ (40 mL) was added at a rate of about 5 mL/hr. The mixture was stirred under an atmosphere of nitrogen overnight, during which time the temperature reached room temperature. The solution was washed with 1% aqueous $AgNO_3$ and filtered to remove the precipitated AgCl. The $CH_2Cl_2$ was dried ($MgSO_4$), filtered, and evaporated in vacuo to yield a yellowish solid. The product was purified by short-path column chromatography on 210 g of >230 mesh silica gel in 10% ethyl acetate/$CH_2Cl_2$. The product was located by TLC and the relevant fractions were evaporated to a yellowish solid which was triturated with 40% ethyl acetate/hexane to afford a white solid. This material was used in the next step without further purification.

(ii)

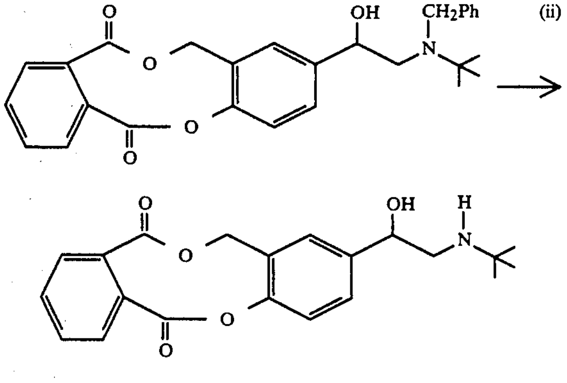

The product from the previous step (0.2 g) was dissolved in a 1:1 mixture of $CH_2Cl_2$ and isopropanol (10 mL). To the stirred solution was added acetic acid (25 μL) and 10% Pd-C (0.02 g). The mixture was hydrogenolyzed at atmospheric pressure for about 20 hr. after which time the catalyst was filtered off and the solvent removed to yield an off-white solid.

The crude product was combined with the product from a second, similar run and was purified by short-path column chromatography over 15 g of silica gel (finer than 230 mesh) made up in 5% MeOH in $CH_2Cl_2$. Two fractions containing the bulk of the product were combined, acetic acid (1.2 equivalents) was added to convert the material completely into the acetate salt, and this material was chromatographed again in $CH_2Cl_2$ in a methanol gradient starting at 1% and increasing to 8% methanol to yield the product, mp. 86°-88° C.

Found, C, 57.86; N, 2.74. Calcd. for $C_{23}H_{27}NO_7 \cdot 2\frac{2}{3}H_2O$, C, 57.85; N, 2.93.

EXAMPLE 2

(i)

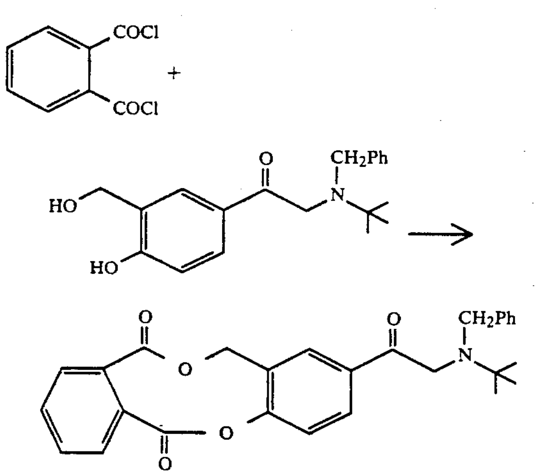

The ketone-diol starting material, as its HCl salt, (10 g) was suspended in dry $CH_2Cl_2$ (400 mL) under an atmosphere of dry $N_2$. To the suspension was added $NEt_3$ (5.745 mL; 1.5 equivs. relative to the HCl salt) resulting in the formation of an amber solution. In a separate reaction flask were placed o-phthaloyl dichloride (4.586 mL; 1.1 equivs. relative to the HCl salt), $NEt_3$ (7.66 mL; 2.0 equivs. relative to the HCl salt) and 4-(N,N-dimethylamino)-pyridine (DMAP; 1 g) all dissolved in $CH_2Cl_2$ (300 mL) and cooled to around −70° C. The first solution was added dropwise to the second solution at such a rate that the internal temperature never rose above −69° C. After about 1.25 h TLC showed that no starting material remained. The reaction mixture was stirred under nitrogen at −70° C. overnight.

MeOH (4.5 mL) was added to the reaction mixture which was then stirred for 0.5 h. Next, AcOH (glacial) was added to neutralise the mixture. The product was washed with $H_2O$, satd. NaCl soln., and dried over $MgSO_4$. After filtration the solvent was evaporated in a vacuum to yield ca. 12 g of yellowish crude product. The product was purified by short-path column chromatography on silica gel using 5% $EtOAc/CH_2Cl_2$ to yield 6.58 g of material which was used in the next step without further purification.

(ii)

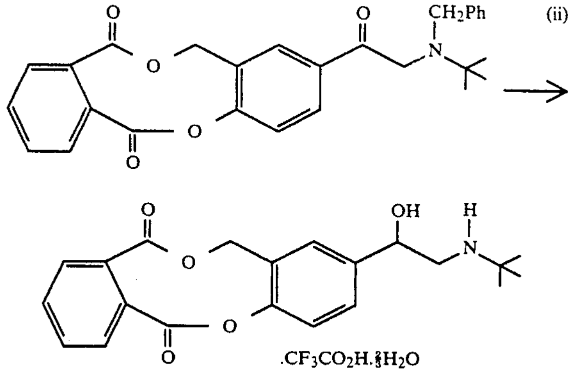

The product from the previous step (6.58 g) was dissolved in $CH_2Cl_2$/isopropanol (132 mL; 1:1 mixture). This solution was added to a hydrogenation flask containing 10% Pd-C (1.316 g) into which was being passed a stream of $N_2$. $CF_3CO_2H$ (TFA; 1.219 mL; 1.1 equivs. based on the substrate) was added with stirring. The reaction suspension was stirred under 1 atmosphere of $H_2$ for about 7 hours. The catalyst was removed by filtration and the solvents were removed by evaporation under vacuum to yield an oil which was purified by short-path column chromatography on silica gel eluting with 10% $MeOH/CH_2Cl_2$. The product from this column was further purified by separation on a second similar column using 5% $MeOH/CH_2Cl_2$ as the eluant. The product was a colorless gum or glass.

Found, C, 55.82; H, 5.10; N, 2.48. Calcd. for $C_{23}H_{24}NO_7F_3 \cdot \frac{2}{3}H_2O$, C, 55.76; H, 5.15; N, 2.83

EXAMPLE 3

Preparation of pyridine-2,3-dicarboxylic acid dichloride

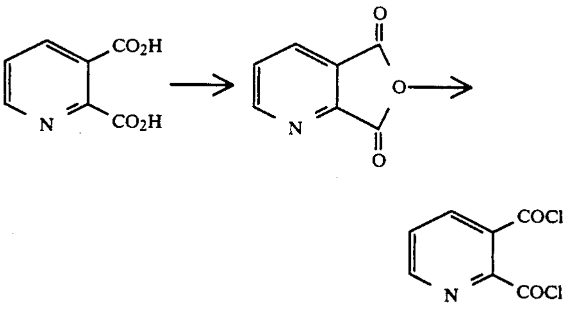

A mixture of pyridine-2,3-dicarboxylic acid (12.5 g) and thionyl chloride (50 mL) was refluxed in an atmosphere of nitrogen for 2 hr. The resulting solution was evaporated to yield a solid, 11.2 g. The product, pyridine-2,3-dicarboxylic anhydride, was taken on to the next step without further purification.

A mixture of pyridine-2,3-dicarboxylic anhydride (11.2 g) and phosphorus pentachloride (18.72 g) was heated in a nitrogen atmosphere at 150° C. for 6 hr. The mixture was allowed to stand at room temperture overnight. $POCl_3$ formed in the reaction was removed by vacuum distillation, and the desired product was collected when the temperture of distillation reached about 100° C. (2 mm Hg). The product was unstable and was stored as −78° C. under nitrogen.

Preparation of 9-[2-[(1,1-dimethylethyl)amino]-1-hydroxyethyl]-7H-[1,6]benzodioxonino[3,4-b]pyridine-5,13-dione, trifluoroacetic acid said

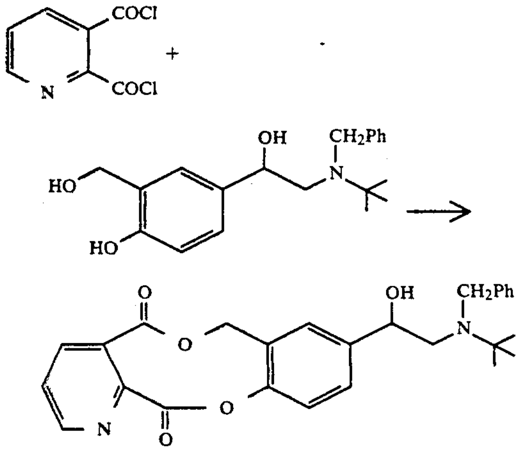

(i)

The di-acid chloride, prepared above, (4.18 g) was dissolved in $CH_2Cl_2$ (300 mL), and the solution was cooled to below −70° C. in an atmosphere of $N_2$. In a separate flash was made up a solution of the triol substrate (6.428 g) and $NEt_3$ (6.28 mL) in $CH_2Cl_2$ (350 mL). This second solution was added dropwise to the first solution over a period of about 21 h. TLC showed that no starting material remained after this time. The organic layer was washed with satd. NaCl soln., dried over $MgSO_4$, filtered, and evaporated under vacuum to yield a tan solid. The crude product was purified by short-path column chromatography over silica gel, eluting with 10% EtOAc/$CH_2Cl_2$. The product was used in the next step without further purification.

(ii)

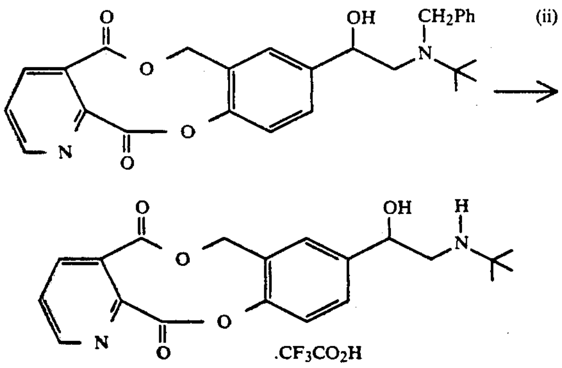

The product from the previous reaction (0.135 g) was dissolved in $CH_2Cl_2$/isopropanol (20 mL; 1:1 mixture). The solution was added to a hydrogenation flask containing 10% Pd-C which was being flushed with $N_2$. The suspension was stirred while $CF_3CO_2H$ (24 μL) was added. The solution was then stirred in an atmosphere of $H_2$ overnight. The reaction was complete as determined by TLC. The catalyst was removed by filtration, and the solvents were removed by evaporation in a vacuum. The crude product was purified by short-path column chromatography on silica gel using $CH_2Cl_2$/5% →10% MeOH. The product was isolated as a solid, mp 153°-155° C. It showed the expected molecular ion for the desired product in the mass spectrum.

EXAMPLE 4

Preparation of 2-[2-[(1,1-Dimethylethyl)amino]-1-hydroxyethyl]-7-methyl-13H-dibenzo[b,g][1,5]-dioxonin-6,11-dione, trifluoroacetic acid salt, hemihydrate.

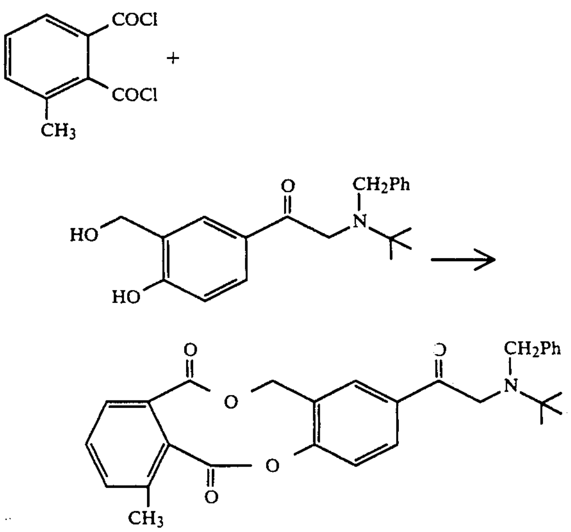

A solution of triethylamine (3.144 mL) and 4-dimethylaminopyridine (DMAP) (410 mg) in dry $CH_2Cl_2$ (150 mL) was stirred under nitrogen and cooled in a Dry-Ice/iso-propanol bath. In a dropping funnel attached to the flask were dissolved 4.11 g of the ketone-diol as its HCl salt and triethylamine (2.32 mL) in dry $CH_2Cl_2$ (200 mL). A solution of 3-methylphthaloyl dichloride (2.7 g) in dry $CH_2Cl_2$ (5 mL) was drawn into a syringe which was then connected to the reaction flask by a needle through a rubber septum. The reagents from the dropping funnel and the syringe were added simultaneously to the cooled reaction flask contents over a period of about 3 hr. The reaction mixture was stored at −78° C. overnight. The reaction was worked up by dilution with $CH_2Cl_2$ (300 mL) and washing with water (2×200 mL). The organic solution was dried ($MgSO_4$), filtered, and evaporated under reduced pressure. The crude product was purified on silica gel (250 g of Flash Chromatography Grade) eluting with 5% ethyl acetate/$CH_2Cl_2$. The desired product from this separation was used in the next step without further purification (ii)

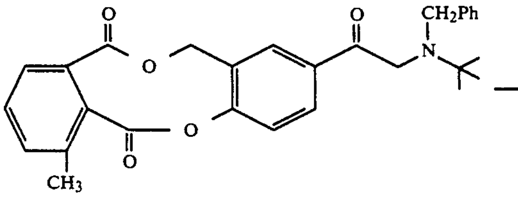

-continued

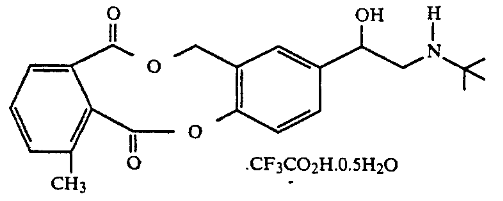

.CF₃CO₂H.0.5H₂O

The N-benzyl derivative (0.31 g) from the above reaction was dissolved in 1:1 isopropanol/$CH_2Cl_2$ (12.4 mL). To this solution was added $CF_3COOH$ (57 μL) and 10% Pd-C catalyst (62 mg). The mixture was hydrogenolyzed at atmospheric pressure for about 28 hr. After filtering off the catalyst, the filtrate was evaporated off and the crude product was purified on Flash Grade silica gel (50 g) in 5% MeOH/$CH_2Cl_2$. The desired product was located by TLC in the fractions eluting from the column. Evaporation led to the product, 197 mg, which showed no sharp melting point, but analyzed correctly:

Found, C, 57.14; H, 5.38; N, 2.66. Calcd. for $C_{24}H_{26}NO_7F_3$. $0.5H_2O$, C, 56.91; H, 5.37; N, 2.76

EXAMPLE 5

Preparation of 8-[2-[(1,1-dimethylethyl)amino[-1-hydroxyethyl]-4H, 6H, 12H-thieno[3,4-c][1,6]benzodioxonin-4,12-dione, trifluoroacetate (i).

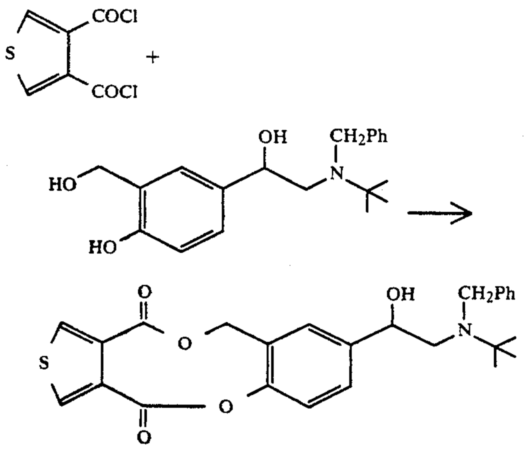

A solution of the triol (128 mg), triethylamine (100 μL), and DMAP (10 mg) was made up in $CH_2Cl_2$ (8 mL) at 0° C. To this was added a solution of the di-acid chloride (90 mg) in $CH_2Cl_2$ (6 mL). The reaction mixture was stirred for 2 hr. at 0° C. then it was diluted with $CH_2Cl_2$ (100 mL). The organic layer was washed with water followed by satd. aqueous NaCl, dried ($MgSO_4$), and evaporated under reduced pressure to yield the crude product (180 mg) which was used without further purification.

(ii).

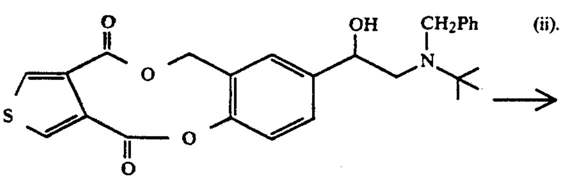

-continued

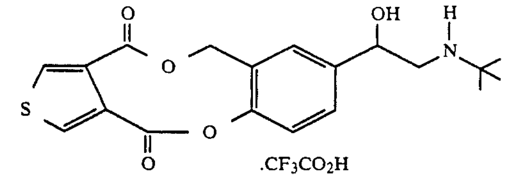

.CF₃CO₂H

The product from the previously described reaction (0.42 g) was dissolved in a mixture of $CH_2Cl_2$/isopropanol (10 mL of 1:1) and was added to a flask containing 10% Pd-C (0.212 g) which was being flushed with $N_2$. Trifluoroacetic acid (0.369 mL; 5.3 equivs. based on substrate) was added while the suspension was stirred. The stirred mixture was hydrogenated at atmospheric pressure overnight. After about 19 h another batch of catalyst (0.212 g) was added because the reaction was incomplete. Reaction was complete after a further 2.5 h under a hydrogen atmosphere. The catalyst was filtered off and the solvents were removed under vacuum. The residue was kept under high vacuum overnight. The crude product was purified by short-path silica gel chromatography eluting with 10% MeOH/$CH_2Cl_2$. The desired product was isolated from the eluate and was subjected to a further purification on a second silica gel short-path column. From this column was obtained 0.11 g of the desired ester as a glass which had no definite mp.

$C_{21}H_{22}NO_7SF_3$. $0.25H_2O$ CALCD FOR C, 51.06; H, 4.59; N, 2.84; S, 6.49 Found C, 51.08; H, 4.75; N2.75; S, 6.15.

EXAMPLE 6 AEROSOL FORMULATION

A suspension aerosol is made according to the following directions. Disperse a suitable surfactant, such as oleic acid, Span 85 (sorbitan trioleate), oleyl alcohol, sorbitan monooleate, or soy lecithin (10 to 400 mg/aerosol can) with agitation in an aerosol holding tank maintained at 30° F. (−2° C.). Add the compound

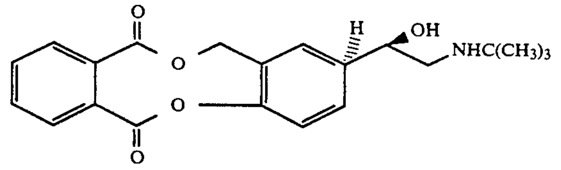

or any other compound of formula I (50 to 400 mg/aerosol can) in micronized form, and continue agitation. Cover the tank and overlay the concentrated suspension/solution with nitrogen. Run the concentrate into the aerosol cans, fit a valve on each can and crimp on to the can. Finally, charge Freon 12 (dichlorodifluoromethane; 12 to 20 g/aerosol can) through the valve. Propellants other than Freon 12, such as Freon 114 (1,2-dichloro-1,1,2,2-tetrafluoroethane) may be used. Any suitable propellants, including those which are not Freon compounds, may also be used.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula

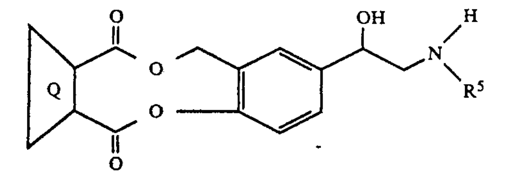

I wherein $R^5$ represents $C_1$ to $C_6$-alkyl or the group—$(CH_2)_n$—Z—$(CH_2)_m$—Ar wherein Z represents O, S or—$CH_2$— and Ar is phenyl, optionally substituted by one or two groups selected from the group consisting of hydrogen, $C_1$ to $C_6$-alkyl, $C_1$ to $C_6$-alkoxy, Cl, F, Br, I, $NO_2$, $CF_3$, CN, $R^6$—$S(O)_x$, $R^7$—CO—, $(R^8R^9)$NCO-and phenyl, wherein x is 0, 1 or 2, and each $R^6$, $R^7$, $R^8$ and $R^9$ is independently $C_1$ to $C_6$ alkyl or two adjacent groups on Ar may form together an additional fused benzenoid ring; n and m independently represent integers of from 1 to 8; and ring Q represents one of the rings $Q_1$, $Q_2$, $Q_3$ or $Q_4$ below:

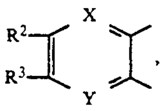

,

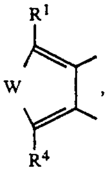

, $Q_1$ $Q_2$

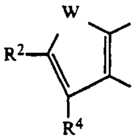

or

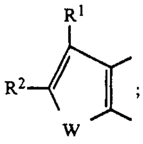

;

$Q_3$ $Q_4$

X is N or C—$R^1$;

Y is N or C—$R^4$;

W represents O or S;

each of $R^1$, $R^2$, $R^3$ and $R^4$ is independently selected from hydrogen, $C_1$ to $C_6$-alkyl, $C_1$ to $C_6$-alkoxy, Cl, F, Br, I, $NO_2$, $CF_3$, CN, $R^{10}$—$S(O)_y$—, $R^{11}$—CO—, $(R^{12}R^{13})$N—CO— or phenyl, wherein y is 0,1 or 2 and each of $R^{10}$, $R^{11}$, $R^{12}$ and $R^{13}$ is independently $C_1$ to $C_6$-alkyl, or, in the ring $Q_1$, two adjacent groups, i.e. $R^1R^2$, $R^2R^3$ or $R^3R^4$, may form together an additional fused benzenoid ring; or a pharmaceutically acceptable acid addition salt thereof.

2. A compound according to claim 1 in the form of a pharmaceutically acceptable acid addition salt.

3. A compound according to claim 2 wherein $R^5$ represents i-$C_3H_7$, t-$C_4H_9$ or —$(CH_2)_n$—Z—$(CH_2)_m$—Ar wherein n and m each independently is an integer of 2 to 6, Z represents O and Ar is phenyl.

4. A compound according to claim 2 wherein Q represents the ring $Q_1$.

5. A compound according to claim 4 wherein $Q_1$ is

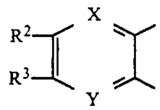

wherein X is N or C—$R^1$, and Y is N or C—$R^4$ with the proviso that X and Y are not both N; each of $R^1$, $R^2$, $R^3$ and $R^4$ is independently selected from hydrogen, $C_1$ to $C_6$-alkyl, $C_1$ to $C_6$-alkoxy, Cl, F, Br, I, $NO_2$, $CF_3$, CN, $R^{10}$—$S(O)_y$—, $R^{11}$ —CO—, $(R^{12}R^{13})$N—CO— or phenyl, wherein y is 0,1 or 2 and each $R^{10}$, $R^{11}$, $R^{12}$ and $R^{13}$ is independently $C_1$ to $C_6$-alkyl, or, in the ring $Q_1$, two adjacent groups, i.e. $R^1R^2$, $R^2$ $R^3$ or $R^3R^4$, may form together an additional fused benzenoid ring.

6. A compound according to claim 5 wherein one or two of $R_1$, $R_2$, $R_3$, and $R_4$ are independently selected from F, Cl, $CF_3$, $CH_3$and $C_2H_5$ and the remainder of these substituents are H.

7. A compound according to claim 3 wherein Q represents the ring $Q_2$.

8. A compound according to claim 3 wherein Q represents the ring $Q_3$.

9. A compound according to claim 3 wherein Q represents the ring $Q_4$.

10. A compound according to claim 6 wherein Q represents the ring.

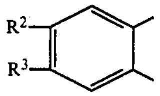

$Q_1$ wherein one of $R^2$ and $R^3$ is hydrogen and the other is H, F, Cl, $CF_3$, $CH_3$ or $CH_2H_5$.

11. A compound according to claim 6 wherein Q represents the ring

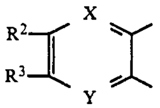

$Q_1$ and wherein either Y is C—$R^4$ and X is N; or X is C—$R^1$ and Y is N and $R^1$ and $R^4$ are H, F, Cl, $CF_3$, $CH_3$ or $C_2H_5$.

12. A compound in accordance with claim 1, of the formula

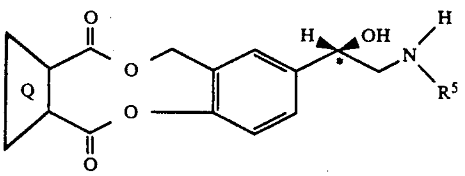

wherein $R^5$ is as described in claim 1.

13. A compound according to claim 10 selected from the group consisting of

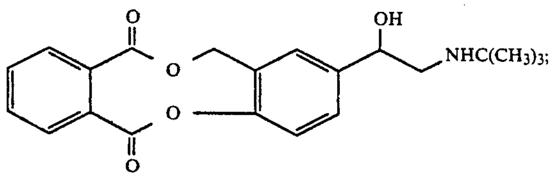

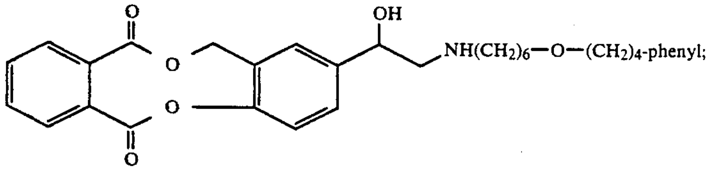

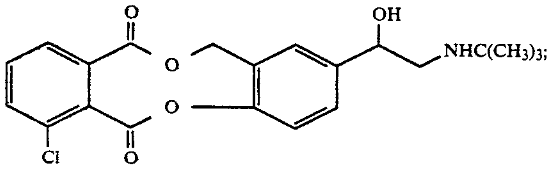

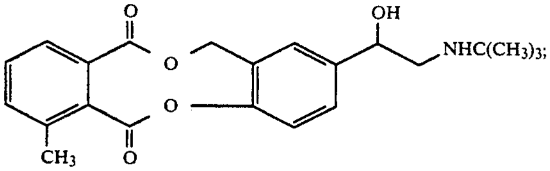

and

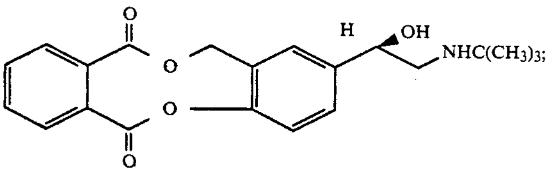

or a pharmaceutically acceptable acid addition salt thereof.

14. A compound according to claim 13,

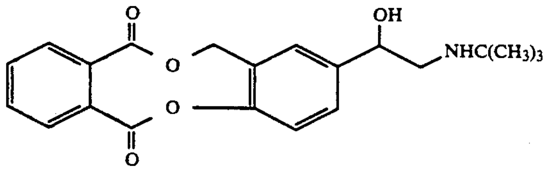

or a pharmaceutically acceptable acid addition salt thereof.

15. A compound according to claim 13 having the structural configuration

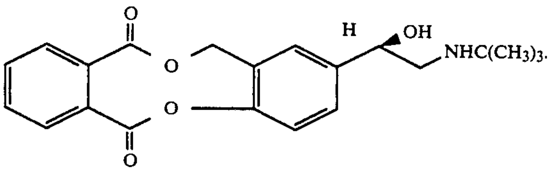

or a pharmaceutically acceptable acid addition salt thereof.

16. A compound according to claim 5

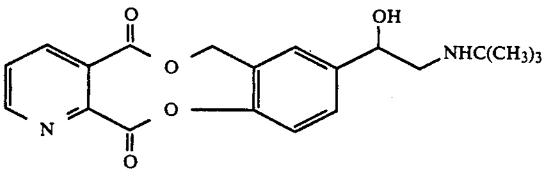

or a pharmaceutically acceptable acid addition salt thereof.

17. A pharmaceutically composition comprising a compound of claim 1, and a pharmaceutically acceptable carrier material.

18. A method of treating asthma, asthmatic bronchitis and other forms of obstructive pulmonary disease comprising administering an effective amount of a compound as defined in claim 1.

* * * * *